United States Patent [19]

Gilak

[11] Patent Number: 4,832,916
[45] Date of Patent: May 23, 1989

[54] CHROMATOGRAPHIC COLUMN FOR IMMUNOLOGICAL DETERMINING METHODS

[76] Inventor: Armin Gilak, Grenzstr. 8, D-5309 Meckenheim, Fed. Rep. of Germany

[21] Appl. No.: 18,085

[22] Filed: Feb. 24, 1987

[30] Foreign Application Priority Data

Mar. 17, 1986 [DE] Fed. Rep. of Germany ....... 3608883

[51] Int. Cl.⁴ ..................... G01N 30/02; G01N 30/48; G01N 33/538
[52] U.S. Cl. ..................................... 422/70; 210/656; 210/658; 436/541; 436/807; 436/810
[58] Field of Search .................... 436/541, 807, 810; 422/70; 210/656, 658

[56] References Cited

U.S. PATENT DOCUMENTS

| | | | |
|---|---|---|---|
| 4,145,406 | 3/1979 | Schick | 436/541 X |
| 4,208,187 | 6/1980 | Givner | 436/807 X |
| 4,425,438 | 1/1984 | Bauman | 436/541 X |
| 4,528,268 | 7/1985 | Andersen | 436/810 X |

Primary Examiner—Sidney Marantz
Attorney, Agent, or Firm—Balogh, Osann, Kramer, Dvorak, Genova & Traub

[57] ABSTRACT

The invention relates to a chromatographic column for separating antigen-antibody complexes from the free antigens not bonded to the antibodies and/or for complete bonding of all marked substances in the immunological determination of antigens or haptens by radio-immunological, luminescence-immunological, fluorescence-immunological or enzyme-immunological determination methods in which a crepe-like tightly rolled filter paper of high degree of purity, in particular of regenerate cellulose, is pressed into a water-proof and water-tight envelope as nonpolar column material. According to the invention the chromatographic upright column comprises an upper reaction portion chargeable from above and a lower separation and measuring portion which are separated from each other by a perforable bottom, the column being fastened from below on the perforable bottom of the column.

10 Claims, 2 Drawing Sheets

CHROMATOGRAPHIC COLUMN FOR IMMUNOLOGICAL DETERMINING METHODS

BACKGROUND OF THE INVENTION

1. Field of the Invention

The invention relates to a chromatographic column for immunological investigation methods.

Such a chromatographic column is intended for separation methods for immunological determinations, in particular fluorescence-immunological, enzyme-immunological or luminescence-immunological investigations, in which the antigen-antibody complex form is separated from the free antigens not bonded to the antibody with the aid of the dry chromatographic column to which the liquid reaction mixture of the immunological determination is introduced, the antigen-antibody complex solution being measured extinction-photometrically.

SUMMARY OF THE INVENTION

The invention has as its object the provision of a particularly economical chromatographic column, easy to handle, for such investigation methods which permits in particularly simple and reliable manner separation and measurement of the substances to be investigated.

This objective is achieved according to the invention in a dry chromatographic column for separating antigen-antibody complexes from the free antigens to bonded to the antibodies and/or for complete bonding of all marked substances in the immunological determination of antigens or haptens by radioimmunological, luminescence-immunological, fluorescence-immunological or enzyme-immunological determination methods in which a crepe-like tightly rolled filter paper of high degree of purity, in particular of regenerate cellulose, is pressed into a water-proof and water-tight envelope as nonpolar column material by the improvement that the chromatographic upright column of filter paper comprises an upper reaction portion chargeable from above and a lower separation and measuring portion which are separated from each other by a perforable bottom, the column being fastened from below on the perforable bottom of the column.

It is achieved with the invention that reaction on the one hand and separation and measurement on the other can be carried out in a single column, possibly without outer contact, and the material to be investigated, in particular the radioactive material, remains completely in the filter and can be measured in extremely simple manner by means of a gamma counter in the case of radio-immunological investigations or photometrically in the case of luminescence-immunological investigations.

An important desired secondary effect in the radio-immunological determinations with the column according to the invention is that in radio-immunological determinations the entire radioactive reaction mixture remains absorbed in the column. After the counting of the sample the radioactivity is thus in a form which is easy to handle; the danger of contamination with residues of the liquid reaction mixture is greatly reduced compared with known methods. Even when the antibody is stationarily bonded to a substrate substance within the test tube the entire liquid radioactivity is absorbed in the column; at the same time the free antigens are bonded in the upper column portion.

Preferably the filter paper column is attached from below tightly to the perforable bottom of the reaction portion chargeable from above. In the perforation a particularly effective penetration and likewise adsorption is achieved on perforation up to the depth of the filter paper. Preferably, the filter paper column can have at the top a funnel-shaped widening with which it is attached in clamping fit beneath the similarly shaped bottom of the column.

The filter paper may be pressed into a plastic sheath which may possibly be surrounded by a metallic sheath, in particular of galvanized copper. The latter is suitable as screening material in the case of extinction-photometric or radio-immunological measurements.

The perforation may also be made from the outside. It is however also possible to equip parts in contact with the bottom with tines, prongs or the like which for instance under pressure on the two ends of the column perforate the bottom (closed system). A particular use of column and filter in automatic devices is also possible with the invention. In this case two tubular microcuvettes closed at the bottom are disposed adjacent each other, the first serving as reaction vessel with perforated cover. The second serves as separating and measuring vessel and contains in the upper portion the column-like filter paper tightly fitted into a plastic sheath and in the lower portion the extinction-photometrical measurement is carried out. Instead of using two microcuvettes a single device is also possible, the reaction portion described with perforable bottom being disposed at the top and the separating and measuring portion at the bottom. The separating portion consists of the filter paper column described above which is widened in funnel-shaped manner at the top and attached in clamping fit beneath the bottom of the reaction portion. The measuring portion is a microcuvette which is also pushed from below over the plastic sheath or sleeve of the reaction portion.

In this embodiment it is possible to lyophilize the reagents, except for the substance to be determined, at low temperatures, in particular beneath $-20°$ C.

Finally, it is possible when using the step according to the invention in automated devices to make all the columns perforable employing a single charging operation, manually or automatically. The charging of the column is from above as in all further developments of the invention.

A particularly expedient important further development of the invention resides in that the crepe-like filter material to increase its bonding affinity is impregnated with an organic acid, in particular maleic or oxalic acid or possibly a base, and the impregnating agent washed out again. This imparts to the paper when dried again an improved absorbability and differentiation of the absorption due to a certain swivelling of the fibres.

BRIEF DESCRIPTION OF THE DRAWINGS

Examples of embodiment of the invention will be described in more detail hereinafter with the aid of the accompanying drawings, wherein.

DESCRIPTION OF THE PREFERRED EMBODIMENTS

Figure 1:
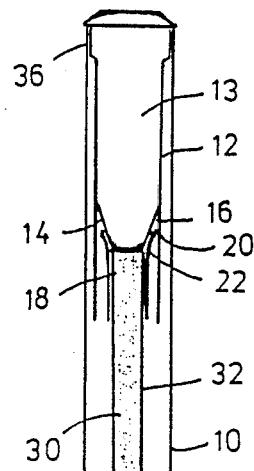
FIG. 1 shows a chromatograhic column for the radio-immunological investigation method (radio-immunoassay:RIA)

FIG. 1 shows for radio-immunological determinations a test tube 10 into which an upright chromatographic column 12 is inserted in tight or sealing manner and comprises substantially in the centre a bottom 14. The column with the exception of the filter paper and the test tube consists of a transparent plastic, preferably polyethylene. The bottom 14 of the reaction vessel is attached firmly and sealed with respect to the column. The bottom 14 is made conical or funnel-shaped towards the bottom at 16 and comprises a thin perforable base 18.

The conicity of the funnel bottom results in a corresponding annular space 20 which is formed from the inner wall of the straight column tube and the outer wall of the funnel-like bottom and tapers to a point at the top. This simple construction is utilized to permit a clamping connection in the manner to be described below.

Complementary to this funnel bottom the filter and measuring portion of the separating vessel comprises a sleeve or sheath which merges into a complementarily funnel-shaped widened portion 22. The sheath may consist of metal but also of plastic. Tightly pressed into the sheath is a filter 30 of prepared crepe paper which forms the actual column material. It comprises an envelope 32 of an outer stiff plastic. The column material may consist of cellulose pretreated with chemical impregnating agents, for example with organic acids, preferably maleic or oxalic acid or possibly with a base. The reaction vessel provided with sheath is inserted into the funnel extension of the column in such a manner that the filter 30 contains the perforable bottom.

In the execution of the sample determination according to the invention the reagents are pipetted into the reaction vessel 13. After setting the reaction equilibrium at the end of the incubation time, with a pointed object the funnel-shaped bottom of the reaction portion is perforated from below or preferably from above, this being done a considerable distance into the crepe filter. The liquid reaction mixture runs through the perforated bottom into the column-shaped filter. When this is done separation takes place in that the unbonded phase, i.e. the free antigens not bonded to antibodies, is absorbed in the upper column portion whilst the bonded phase, i.e. the antigen/antibody complex, migrates into the lower column portion. All the radioactive liquid is absorbed by the filter paper enclosed in water-tight manner and can thus be easily dispensed without any danger of contamination. Of course, in the test execution the tube may be closed with a cover 40. Due to the close bearing of the filter material on the bottom of the reaction vessel and the continuous perforation excellent wetting of the entire column material 30 is ensured. Other possibilities of the vertical fixing of the filter paper with sheath within the entire column are of course possible, such as small ribs on the one part, recesses on the other part, an annular bead on the funnel-shaped bottom and an annular groove on the widened sheath, etc. It should be added that the upper column portion, the reaction vessel 13, is fitted via a widened portion 36 (fitting collar) into the sheath tube 10.

Figure 2:
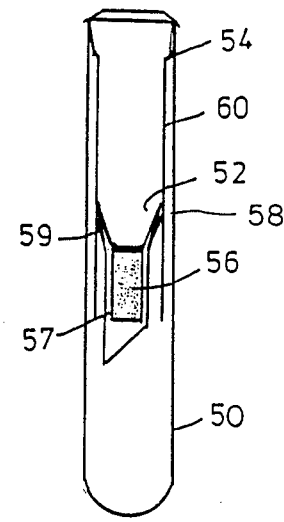
FIG. 2 shows a chromatographic column for example for fluorescence-immunological or luminescence-immunological investigation methods.

FIG. 2 shows an example of embodiment, particular for luminescence-immunological, fluorescence-immunological and enzyme-immunological investigation methods. In a sheath tube 50 a similar construction as in FIG. 1 in the form of a column with column head 54 fitting closely against the sheath tube inner side is inserted.

Figure 3:
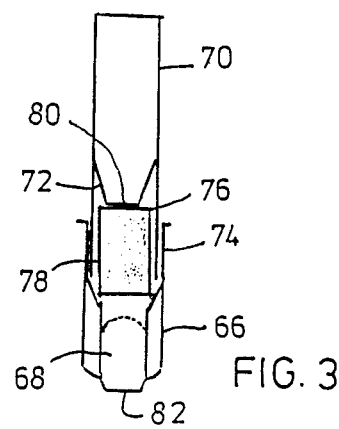
FIG. 3 shows an embodiment with microcuvette.

Whereas in the design of FIG. 1 the sleeve widening of the long filter is substantially in metal over a relatively short section, for the luminescence method only a short piece of filter 56, possibly with plastic outer sheath, is held in for example a long metallic sheath tube 57. A widened sleeve 59 consisting for example of plastic is attached in a similar manner to FIG. 1 over the complementary funnel-shaped bottom 58 of the column. However, in this case the widened sheath/shield 59 extends right to the top at the intermediate or annular space formed between the inner side of the straight column tube and the outer side of the funnel-shaped bottom 58 and is contained snuggly fitted in the latter on slight application pressure. The possibly metallic sheath tube 57 consisting of galvanized copper for locating the filter serves as shield. In the illustration the column is cut inclined at the bottom to ensure in constrained manner a dripping of the liquid possibly present only in small quantities. Embodiments without a shield 59 are also possible. The filter paper can also be pressed into the capillary sheath. For fluorescence-immunological investigation the reagents are pipette into the reaction portion 60 of the chromatographic column, including the marking substance. After setting the reaction equilibrium the funnel-shaped bottom of the reaction portion is perforated up to the filter paper lying closely therebelow and the liquid reaction mixture flows from above into the filter column. When this is done the components are separated in that the free phase is bonded i the upper column portion and the bonded phase, i.e. the antigen/antibody/complex to be measured, passes through the separating column and drips down onto the bottom of the test tube where it can thus be measured by extinction photometry. The shield 59 can be coloured. FIG. 3 shows an embodiment comprising a measuring cuvette 66 which is formed as microcuvette and in order to be usable for very small amounts of filtered liquid has a constriction in the lower region 68. Of interest is that the same column 70 with practically the same funnel-shaped bottom 72 as described with regard to FIGS. 1 and 2 fits into said measuring cuvette and is simply inserted with its lower open end 74. In this case the filter material 76 is pressed into a plastic sheath 78 which bears closely on the perforable bottom 80 of the funnel-shaped reaction vessel. The reaction vessel can once again be sealed by a cover 40. As in FIG. 1 the lower end of the sheath tube, in this case the microcuvette forms the measuring vessel and the column 70 the reaction and separating vessel. The antigen/antibody/complex can again be measured photometrically. In this case no separate shield is provided but this can be done. The microcuvette is a design with particularly small bottom 82 for measuring technical reasons.

Figure 4:
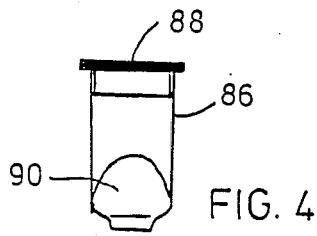
FIGS. 4/5 shows reaction vessel and measuring vessel for automated devices.
Figure 5:
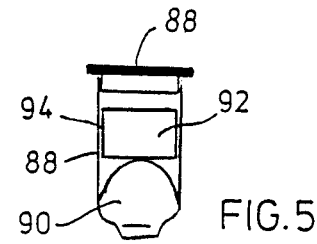

The microcuvettes 86 and 88 of FIGS. 4 and 5 are particularly suitable for automated apparatuses. The microcuvette 86 forms the reaction vessel and the microcuvette 88 of FIG. 5 the measuring vessel.

The microcuvettes may for example be arranged grouped in racks. In the measurement the reaction vessel is then omitted and the measurement carried out in the measuring vessel only. The two vessels are closed by tightly selling attachable covers 88. The microcuvettes are again constricted at the bottom, firstly to fit properly into the holder of the automatic device and secondly to enable even very small defined volumes to be measured, as can be seen at 90. In specimen investigation by immunological methods, in particular in fluorescence-immunological determinations, pipetting of the reagents into the microcuvette 86 as reaction vessel is carried out in a specific sequence. At the end of the incubation time the reaction mixture is aspirated and transferred to the filter in the measuring cuvette 88. When the liquid passes through the column-like filter the components are separated as described with reference to FIGS. 2 or 3. The liquid on the bottom of the measuring cuvette contains the antigen/antibody/complex and can be photometrically measured. The microcuvette 88 can have the same for as the microcuvette 86 of FIG. 4. The filter may be of the same material as already described and explained in further detail below. The filter material here is placed in a sheath 94 consisting for example of plastic and completely filling the internal periphery of the microcuvette 88.

Thus, according to the invention the reagent is introduced from above into the chromatographic column described, filtered and separated in the centre portion and the measurement is carried out at the bottom. The column material is a dry adsorption agent of nonpolar material in the form of a homogeneous felted crepe-like filter paper of high degree of purity rolled to form a tight column. The filter paper consists of pure linters having a polymerisation degree of 2000–3000 or of regenerate cellulose having a polymerisation degree of 800–3000 and is free of soluble substances. The filter paper has a uniform texture with bores of the order of magnitude of 1–14 $\mu$m and has a uniform absorbability over the height of the column. To increase the bonding affinity the filter paper is treated with acids, preferably maleic or oxalic acid, and possibly also with bases. The separation is carried out rapidly and extremely precisely by the cooperation of gravity and capillary forces. The separation takes place surprisingly in such a manner that the low-molecular components (free antigens and antibodies) are bonded i the upper column portion, i.e. after a short running time, whilst the high molecular antigen-/antibody/complexes migrate through the column unbonded. In FIG. 1, with a column sealed at the bottom, the complexes remain in the lower column portion. In FIG. 2 with the column open at the bottom the complex is contained in the liquid dripping down at the bottom. Presumably, with the nonpolar adsorption agent van der Waals' and hydrophobic interactions predominate by which the migration behaviour can be explained.

In all the embodiments all reagents can be lyophilized in the column except for the substance to be determined.

The embodiments of FIG. 1 for radio-immunological determination includes a metal shield in the upper filter portion so that only the radioactivity of the antigen/antibody/complex disposed at the bottom is measured. Similarly, the embodiments for fluorescence-immunological or luminescence-immunological investigations (FIGS. 2, 3 and 5) include a shield of plastic round the column-like filter paper to avoid any light reflection.

Figure 6:
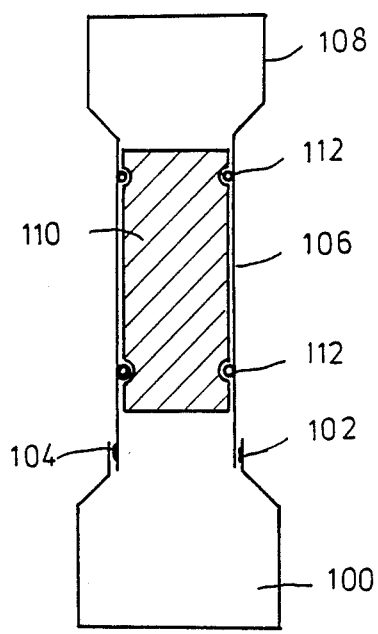
FIG. 6 shows a further embodiment.

Another possibility of carrying out a method according to the invention (FIG. 6) is to use a reaction vessel 100 of a material as mentioned above possibly after fitting a cap which is not illustrated. After the reaction in the vessel 100 an addition of the marking substances the filter and separating portion 106 is attached tightly to the neck 102 of the reaction vessel. Seals 104 are indicated for this purpose. However, any other form-locking connection providing good sealing may be employed. A filter 110 of the type described above is tightly pressed into the separating and measuring portion 106. The pressing action may be increase by ribs 112 which are only indicated and which can be provided at the top and bottom. The measuring and separating portion is continuous, i.e. the previously mentioned perforable bottom is omitted. After fitting on the entire unit is turned through 180° (turned upside down). The solution runs through the filter prepared in the aforementioned manner. The measurement is as described above. The separation of head and bottom portion can of course be at another point, for example near the lower section of the reaction vessel 108 or at any other convenient point.

The apparatus is preferably made available as kit, containing the chromatographic column and the usual known reagents for a specific test method, possibly in measured unit amounts.

The measuring apparatus can be formed again like the microcuvette of FIG. 5 (without bottom to be perforated) and made so that it can be connected in plug-type manner to the reaction vessel.

Finally, it is also possible, for example for automated apparatuses, to perforate a whole series of columns by pressing them on for example simulaneously. This may for instance be done by hand or via a plate. For this purpose for example the cover can be provided with long pointed prongs. The perforation is done by applying pressure to the cover. It would however be necessary in this case to make the "column" adequately stiff. The funnel-shaped bottom of the column is made substantially pre-weakened.

I claim:

1. Chromatographic column comprising means for separating antigen-antibody complexes from the free antigens not bonded to the antibodies and/or for complete bonding of all marked substance in the immunological determination of antigens or haptens by radioimmunological, luminescence-immunological, fluoresce-immunological. or enzyme-immunological determination methods, said chromatographic column being inserted in a sealing manner in a test tube and comprising an upper potion defining a reaction vessel for receiving reagents, a tightly roller filter material of high degree purity, an envelope made from water-proof and water-tight material tightly encompassing said filter material, said envelope encompassed filter material being secured in the lower portion of said column, said lower portion of said column defining a separation and measuring portion, and a perforable bottom member separating said reaction vessel from said encompassed filter material, whereby upon perforation of the bottom member, the reagents in the reaction vessel will flow through the filter material.

2. Chromatographic column according to claim 1, wherein the filter material is pressed into a plastic sheath which is surrounded by a metallic sheath, in particular of galvanized copper.

3. Chromatographic column according to claim 1, including a fitting collar at the upper end of the reaction vessel for inserting said column into a plastic test tube.

4. Chromatographic column according to claim 1, wherein the filter material portion of the column to increase its bonding affinity is prepared by chemical impregnating agents such as organic acids, in particular maleic acid or oxalic acid or possibly a base.

5. Chromatographic column according to claim 1, comprising a lower reaction vessel with attachable filter and measuring portion in which, tightly pressed crepe filter material is disposed which tightly closes the wall and is disposed in a sheath to increase the bonding affinity of said filter material, the column being tunable through 180° and placed upside down for the separating and measuring operation.

6. Chromatographic column according to claim 1, wherein two tube-like microcuvettes closed at the bottom are disposed adjacent each other, and as reaction vessel a column top is used or formation of the microcuvette itself as reaction vessel with performable cover, and on the second microcuvette a separating or measuring column top is disposed with a column of filter paper or insertion of the filter only into the second microcuvette, luminescence measurements taking place in each case solely at the second microcuvette.

7. Chromatographic column according to claim 1, wherein the filter material comprises a regenerated cellulose.

8. Chromatographic column according to claim 1, wherein the upper portion of the envelope carries at the top and outside a funnel-like widening with which it is fastened in a clamping fit beneath the bottom member material is pressed into a plastic sheath which is surrounded by a metallic sheath, in particular of galvanized copper.

9. Chromatographic column according to claim 8, wherein the filter material portion of the column is surrounded by plastic, as an adapting member to a column inner wall with which it is clamped against a conical-shaped bottom of the reaction vessel.

10. Chromatographic column according to claim 9, wherein the filter portion of the column is shielded from the bottom of the reaction portion in particular for photometric measurements, a conical-like widened shield consisting of a perforable bottom conical-shaped towards the bottom.

* * * * *